United States Patent [19]
Turkel

[11] Patent Number: 5,354,296
[45] Date of Patent: Oct. 11, 1994

[54] ELECTROCAUTERY PROBE WITH VARIABLE MORPHOLOGY ELECTRODE

[75] Inventor: David Turkel, Miami, Fla.

[73] Assignee: Symbiosis Corporation, Miami, Fla.

[21] Appl. No.: 36,458

[22] Filed: Mar. 24, 1993

[51] Int. Cl.[5] .......................................... A61B 17/36
[52] U.S. Cl. ...................................... 606/41; 606/49; 606/40
[58] Field of Search ............................ 606/32, 37–41, 606/45–52; 128/642

[56] References Cited

U.S. PATENT DOCUMENTS

| | | | |
|---|---|---|---|
| 4,003,380 | 1/1977 | Wien | 606/51 |
| 4,054,143 | 10/1977 | Bauer | 606/52 |
| 5,234,429 | 8/1993 | Goldhaber | 606/39 |

Primary Examiner—Stephen C. Pellegrino
Assistant Examiner—Michael Peffley
Attorney, Agent, or Firm—David P. Gordon

[57] ABSTRACT

Several embodiments of an electrocautery probe with a variable morphology electrode are disclosed. In one embodiment, the probe has two arms and the electrode is attached to distal ends of the arms. Movement of the distal ends of the arms relative to each other changes the morphology of the electrode. Several electrode embodiments and several ways of moving the distal ends are also disclosed. In another embodiment the electrocautery probe with a variable morphology electrode includes a hollow probe arm within which the electrode is mounted for movement relative to the hollow probe arm. Movement of the electrode relative to the hollow probe arm changes the morphology of the electrode. Several electrode embodiments for use with the hollow probe arm are disclosed.

20 Claims, 9 Drawing Sheets

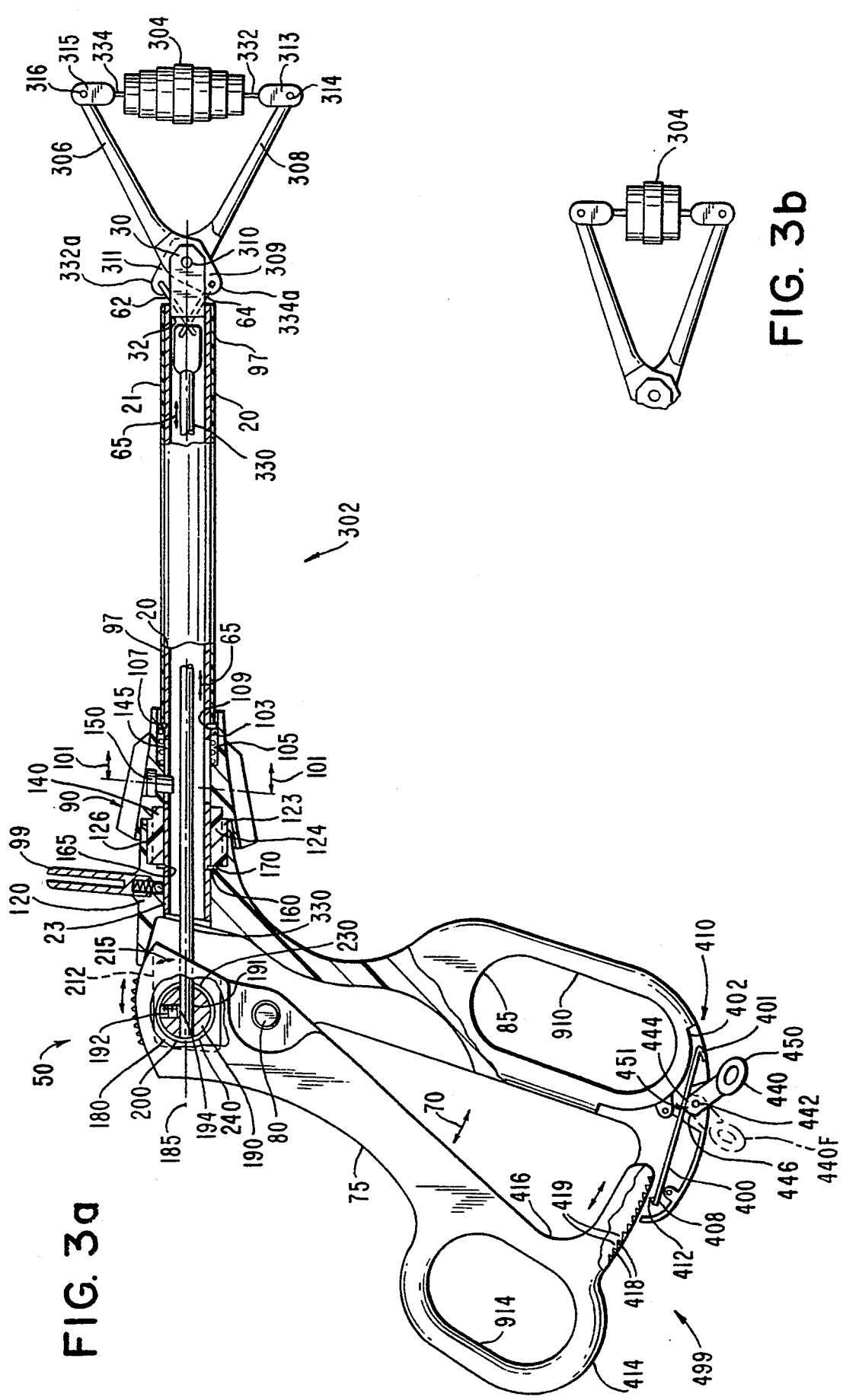

ELECTROCAUTERY PROBE WITH VARIABLE MORPHOLOGY ELECTRODE

This invention relates to commonly owned Ser. Nos. 07/680,389, 07/780,076, and 07/989,984 (which a continuation of 07/833,842), which are all hereby incorporated by reference herein in their entireties.

BACKGROUND OF THE INVENTION

1. Field of the Invention

This invention relates generally to medical instruments. More particularly, this invention relates to an electrocautery probe which has an electrode of adjustable shape and/or size. The invention finds particular application in endometrial ablation and other electrocautery procedures.

2. State of the Art

Endometrial ablation is an alternative procedure to hysterectomy for women with menorrhagia (abnormal or excessive uterine bleeding). In the past, various methods of ablation, including cryosurgery and laser surgery, have been used. More recently, electrocautery techniques have also been used. Endometrial ablation by electrocautery is usually accomplished with a resectoscope and a coagulation electrode mounted on the distal end of an electrocautery probe. The resectoscope includes a telescope for viewing the interior of the uterus, a handle assembly commonly referred to as the working element, and an outer sheath. The working element is generally capable of sliding the probe with a distally mounted electrode axially through the telescope. The outer sheath is placed into the uterus prior to introducing the other elements of the resectoscope.

The actual endometrial ablation procedure involves applying a cauterizing voltage to the electrode and moving the electrode slowly over the entire endometrium (uterine lining) while viewing through the scope. Thermal energy is applied to the endometrial lining of the uterus by the electrode so that the endometrium is destroyed by cauterization and subsequently scars. In order to effect complete destruction of the endometrium, the electrode is moved in a systematic manner, generally beginning at the Fallopian tube ostia (mouth), proceeding to the fundus (above the uterine tubes), and continuing on the anterior, posterior, and lateral uterine walls down to the internal os of the cervix. It is well known, however, that the uterine cavity has acute corners (the cornua and tubulo-interstitial areas) as shown by reference 102 in FIG. 1 and that a relatively small electrode must be used to effectively cauterize these portions of the endometrium. Other portions of the uterus, however, are relatively broad (104 and 106 in FIG. 1) and the use of a small electrode in these areas is tedious and time consuming.

Known electrodes for use in resectoscopes are available in many different shapes and sizes. U.S. Pat. No. 4,917,082 to Grossi et al., for example, discloses several embodiments of a "Resectoscope Electrode" including a coagulating electrode, a knife electrode, a punctate electrode, and a roller electrode, among others. Electrodes for use with resectoscopes are also widely available from Olsen Electrosurgical, Inc., Concord, Calif. They are available as blades, needles, balls, loops, spear tips, flexible wires, semi-circular wires, hooks, spatulas and blunt tips.

Recently, the generally preferred electrode for use in endometrial ablation is the roller (often referred to as "roller bar" or "roller ball") electrode depicted in prior art FIGS. 2a-2c. Such roller ball electrodes are available from Richard Wolf Medical Instruments Corp., Rosemont, Ill. or from Olympus Corp., Lake Success, N.Y. The roller bar 202 or roller ball 204 is approximately 2.5 mm long (e.g., 2.5 mm in diameter for the ball) and, as shown in FIGS. 2a-2c, is mounted on the distal end of an electrocautery probe 206. The distal ball or bar is supplied with a cauterizing voltage through conductors 208, 210 in the probe and is rolled across the endometrial surface methodically until all areas of the endometrium have been cauterized. Because of its small size, the ball or bar fits easily into the acute corners of the uterus. Its relatively small size, however, also renders it inefficient when used in the other portions of the uterus.

While it is possible to change electrodes during the ablation procedure, the changing of electrodes adds time to the procedure, increases the chance that the entire endometrium will not be properly ablated, and requires that a plurality of tools which are typically disposed of after use be utilized. Moreover, it has not been the general practice to change electrodes during the ablation procedure. Thus, by using such a small electrode throughout the uterus, the ablation procedure takes longer and the chance of missing one or more portions of the endometrium is enhanced. Similar problems exist in other electrocautery procedures where an electrode of one shape or size is necessary for part of the procedure but is inefficient or inapplicable for another part of the procedure.

SUMMARY OF THE INVENTION

As used herein, the term "morphology" refers to the shape and/or size of an object, such as an electrode.

It is therefore an object of the invention to provide an electrode for use in electrocautery procedures where the morphology of the electrode is adjustable.

It is another object of the invention to provide an electrocautery probe having means for easily and rapidly adjusting the morphology of the electrode while the electrocautery probe is inserted in a resectoscope.

It is a further object of the invention to provide a rolling electrode on an electrocautery probe where the morphology of the rolling electrode is adjustable while inserted in a resectoscope.

It is also an object of the invention to provide an electrocautery probe with an electrode having a variable surface area and where the surface area of the electrode is adjustable while the electrocautery probe is inserted in a resectoscope.

In accord with these objects which will be discussed in detail below, the electrocautery probe of the present invention broadly includes an electrode of variable morphology mounted at the distal end of a probe, with actuation for adjustment means means is operable from a proximal end of the probe for changing the morphology of the electrode, and means for applying a voltage across the electrode. Numerous embodiments of variable morphology electrodes and being of adjusting means are provided. Among the electrodes which vary in shape and or size are: a volute spring electrode or an electrode formed of cylinder elements rotatably mounted between two arms where movement of the arms relative to each other changes the morphology of the electrode; an electrode constructed of a plurality of beads mounted on a springy wire attached to two arms where movement of the arms relative to each other changes the morphology of the electrode; a plurality of loop electrodes slidably mounted inside a cylindrical probe where sliding the loops into and out of the probe changes the morphology of the electrode; an electrode constructed of a band of tapering width, one end of which is connected to an arm and the other end of which is slidable into and out of a cylindrical arm, where sliding the band into and out of the cylindrical arm changes the morphology of the electrode; and an electrode composed of a plurality of C-shaped springy conductors, legs of which are inserted into cylindrical arms and where sliding the conductors into and out of the arms changes the size and/or shape of the electrode.

The actuation mechanisms for adjusting the morphology of the variable morphology electrode are also varied. These mechanisms include means for moving one or two arms holding an electrode toward each other such as an actuating lever coacting with scissor arms; a sliding loop or a wedge member; a thumb wheel coacting with the sliding loop or wedge member or scissor arms. Alternatively, the actuation/adjusting mechanism can be a mechanism such as disclosed in the parent application hereto with an actuating member including a rod, a clevis, and a means coupling the rod to the arms. For the adjustable morphology electrodes which slide in and out of the cylindrical arm, the mechanism for adjustment preferably includes means for axial movement of the proximal end of the electrode. The means for axial movement typically comprises a push rod activated by a lever, a thumbwheel or the like.

Additional objects and advantages of the invention will become apparent to those skilled in the art upon reference to the detailed description taken in conjunction with the provided figures.

BRIEF DESCRIPTION OF THE DRAWINGS

FIGS. 3a and 3b show schematic side views of one embodiment of the invention.

DETAILED DESCRIPTION OF THE PREFERRED EMBODIMENTS

Figure 1:
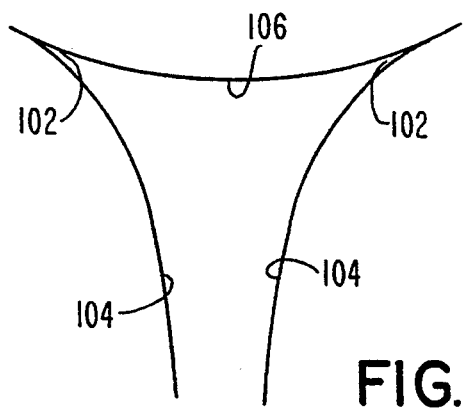
FIG. 1 is a schematic view of the uterine walls showing the acute angles and broad portions of the endometrium.
Figure 2A:
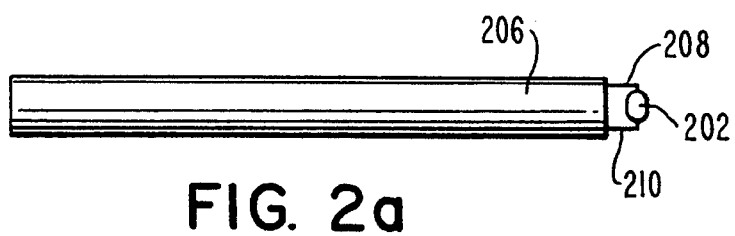
FIGS. 2a and 2b show top view schematics.
Figure 2B:
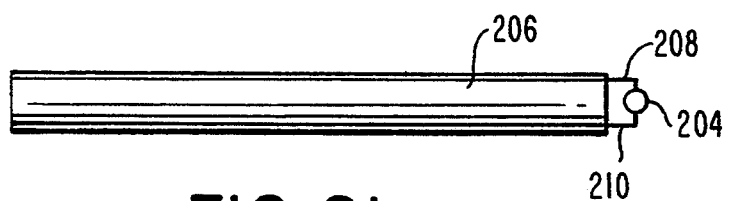
Figure 2C:
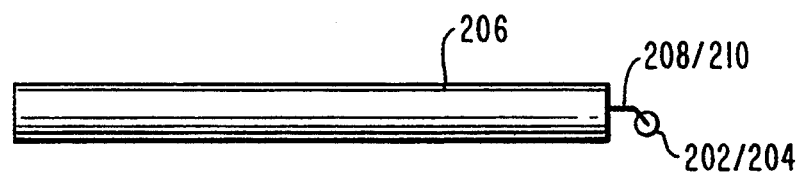
FIG. 2c shows a side view schematic of prior art roller ball and roller bar electrodes.

Referring now to FIGS. 3a and 3b, the electrocautery probe comprises two arms 306, 308 having a pivot point 310 near their proximal ends 311, 309. The distal ends 315, 313 of the arms 306, 308 are provided with additional pivot points 316, 314. Telescoping electrode 304 is mounted for rotation between the distal ends 315, 313 of the arms 306, 308 and coupled with electrode leads 334, 332. The electrode leads 334, 332 are insulated from and fed through the arms 306, 308 to voltage connections 334a, 332a at the proximal ends 311, 309 of the arms 306, 308. Electrode 304 is adjusted by movement of the distal ends 315, 313 of arms 06, 308 relative to each other. Movement of the distal ends of the arms in this embodiment is accomplished by a clevis means 30, actuating apparatus 50, and a push rod 330. The clevis means 30 is advantageously a separately formed aluminum piece which fixedly engages aluminum tube 20 at a distal end 21 of the aluminum tube, e.g. by crimping of tube 20 as indicated at 32. The clevis 30 also engages the probe arms 306, 308 at pivot point 310, as the probe arms pivot around the pivot point 310. The probe arms are also coupled at their proxial ends to the distal end of push rod 330 via coupling elements 62, 64. As is discussed more fully in related application Ser. No. 07/680,389, now U.S. Pat. No. 5,275,612, the clevis effectively translates the reciprocal motion (shown at 65) of the push rod 330 into movement of the probe arms together or apart. Also, as discussed more fully in related application Ser. No. 07/680,389, now U.S. Pat. No. 5,275,612, metal tube 20 is provided with an insulating plastic shrink wrap layer 97 which provides protection when electrical energy is applied at terminal 99 for cauterization procedures.

The reciprocal movement of push rod 330 back and forth, as indicated at 65 in FIG. 3, imparts pivoting or rotational motion to probe arms 306, 308. The reciprocal motion 65 of push rod 330 is effected by the lever action motion 70 of lever arm 75, of the actuating apparatus 50, which is pivotally engaged by means of pivot rod 80 to handle member 85. Handle member 85 and lever arm 75 are configured for one-hand operation. The actuating apparatus 50 can be rotated to any convenient orientation, and back and forth, through 360°, without causing any rotational movement of the probe arms 306, 308 or electrode 304.

Actuating apparatus generally comprises a sleeve (ferrule) member 90, the handle means 85 and the lever arm 75. The sleeve member 90 surrounds a portion of metal tube 20 which is remote from the probe arms 306, 308 and which is just forwardly adjacent to the proximal end 23 of metal tube 20. Sleeve member 90 is movable axially back and forth along metal tube 20 as indicated at 101 of FIG. 3a. However, sleeve member 90 is restrained in it movement by a resilient spring or biasing means 103. Resilient spring 103 is shown as a coil spring peripherally surrounding metal tube 20 and seated in an inner peripheral slot or undercut section 105 of sleeve 90. The resilient spring 103 is held in compression by a retaining ring 107 an an inwardly projecting portion 95 of the sleeve member 90. The retaining ring 107 is seated in peripheral slot 109 of metal tube 20. Alternatively, the retaining ring 107 can be fixedly engaged to the metal tube 20 in the absence of such a peripheral slot. With the provided arrangement, sleeve 90 is coupled by resilient spring 103 to hollow tube 20 and is urged thereby toward the proximal end 23 of the metal tube 20.

As shown in FIG. 3a, metal tube 20 is preferably provided with a plurality of axially extending peripherally spaced apart disposed slots 145 (although only one such slot is required) in a portion of the tube 20 surrounded by sleeve 90. One or more guide rods or inwardly extending protrusions 150 are seated in sleeve 90 and extend therethrough to slidably engage the axial slots 145. With this mating engagement, sleeve 90 is restrained from rotation about metal tube 20, but is movable axially as indicated at 101 in FIG. 3a.

Handle member 85 has a hollow distal portion 120 in the form of a bore coaxial with metal tube 20. Attached internally to the distal portion of handle 85 is a ring 124 which extends loosely around the tube 20. Ring 124 has a peripheral outer surface portion having integral ribs 123 which engage and are preferably sealed (e.g. by gluing) in slots 126 of hollow-bore portion 120 of handle 85. Thus, ring 124 is fixed relative to the handle 85. In order to prevent handle 85 from sliding off the proximal end of tube 20, a retaining ring 160 is provided. Retaining ring 160 is seated in slot 165 of metal tube 20 and sits adjacent the proximal end of ring 124 and in slot 170 of handle member 85. Metal tube 20 is free to rotate in ring 124 as it is only slidably engaged therewith and slightly spaced therefrom.

To enable the rotation of the metal tube 20, probe arms 306, 308 clevis means 30, sleeve 90, etc. with respect to the lever arm 75 and handle 85, some mechanism for permitting rotation of the push rod 330 which is coupled at its proximal portion 180 to the lever arm 75 is required. One embodiment of a push rod coupling means is shown for accomplishing the relative rotation. In particular, the push rod coupling means is shown as a generally spherical surfaced element 190. Spherical element 190 is coaxial to push rod 330 and includes a diametrically located bore 191 through which push rod 330 extends. Push rod 330 is coupled to the spherical element 190 suitably by means of a recessed set screw 192 which threadably engages spherically surfaced element 190 and bears against and frictionally engages push rod 330 at 194.

In order to accommodate a spherical push rod coupling element, the lever arm 75 is provided with a cylindrical bore 200. Bore 200 is parallel to pivot rod 80 which engages the handle member 85 to the lever arm 75, and is transverse to the push rod 330 and the longitudinal axis 185 of metal tube 20. cylindrical bore 200 has a diameter just slightly larger than that of element 190 and closely encloses spherically surface element 190.

A slot 210 is provided in lever arm 75. Slot 210 transversely intersects the cylindrical bore 200 and receives push rod 60. The slot 212 is dimensioned to accommodate the displacement indicated at 215 of push rod 330 during movement of lever arm 75 and the spherically surfaced element 190. The bore 200 in lever arm 75 is suitably open at least on one side of the lever arm 75 to facilitate assembly and engagement of the push rod 330 with spherically surfaced element 190. A closely fitting cap is preferably provided to close the bore and closely secure the spherical element 190 therein.

In operation, the pivotal movement of lever arm 75 as indicated at 70 in FIG. 3a causes the spherically surface element 190 to slidably bear against and contact the forward surface 230 of bore 200, or the rearward surface 240 of bore 200. In this manner, the engaged push rod 330 is moved backward and forward to impart the rotational motion to arms 306, 308 about pivot point 310. When it is desired to change the rotational orientation of the actuating mechanism 50 (comprising handle member 85 and pivotally engaged lever arm 75), the sleeve member 90 is moved away from the rearward end 23 of metal tube 20 (i.e., distally), toward the probe arms against the force exerted by resilient spring 103. When sleeve member 90 is moved in that way, handle member 85 in the disengaged position, the actuating mechanism 50 (handle member 85 and pivoted lever arms 75) is rotatable about metal tube 20 (and vice versa) to any desired position (from 0° to 360°). When the desired amount of rotation is obtained, sleeve 90 is released, and spring 103 forces sleeve 90 back into engagement with handle member 85 with the respective tooth-like elements and slots of the ring and the sleeve mating with each other.

A ratchet mechanism is also provided in FIG. 3a to enable the probe arms 306, 308 to be locked in any of many positions (two such positions being shown in FIGS. 3a and 3b such that further movement of the probe arms toward each other is permitted, but further movement of the probe arms away from each other is not permitted except if the ratchet mechanism is purposely unlocked. The ratchet mechanism comprises a cantilevered resilient strip 400 with a locking barb 412, where the strip 400 is located on the handle 85 and a ratchet element 499 located on the lever 75. The ratchet element 499 has a plurality of teeth 419 radially displaced from a pivot 80 coupling the handle and lever. The teeth 419 have edge surfaces 418 on parallel axes which are parallel to the axis of the pivot 80. A camming lever means 440 is provided in a first position forces the locking barb 412 into contact with the ratchet 499, and in a second position does not force the locking barb 412 into contact with the ratchet 499. The edge of the teeth 419 of the ratchet 499 are preferably located along an arc of a circle having its center point being the pivot 80 which couples the handle and the lever.

The cantilevered resilient strip or leaf spring 400 has a downwardly extending punched out barb 401 for fixing the resilient strip 400 in the handle 85 and an upwardly extending barb or locking element 412 for mating with the ratchet 499 in the lever member 75. Locking element 412 is preferably punched out of the resilient strip 400 and preferably makes a forty-five degree angle relative thereto. Locking element 412 preferably has an edge surface which is parallel to the axis of pivot 80. The resilient strip 400 is inserted into a slot 402 in handle member 85 with the downwardly extending barb 401 extending into slot 402 of the handle member 85 so the resilient strip 400 is engaged in the handle member 85.

As seen in FIG. 3a, the resilient strip 400 is preferably positioned at the portion 410 of handle member 85 which extends furthest and is most remote from the pivotal engagement 80 of lever arm 75 with handle member 85. Likewise, the resilient strip 400 extends at its free end portion 408 toward the portion 414 of the lever arm 75 which is most remote from pivotal engagement 80. By providing the ratchet mechanism at a distance from the point of pivotal engagement 80, finer resolution of possible locked positions is obtainable, as the arc segment for one degree of rotation is larger than an arc segment for one degree of rotation which would be located along an arc closer to the pivot point 80.

As aforementioned, the ratchet mechanism of the invention includes a ratchet 499 including teeth 419 and grooves 418 in the lever arm 75. As seen in FIG. 3a, an elongate arm 416 extends fro lever arm 75 adjacent its remote portion 414. The elongate arm 416 includes the plurality of teeth 419 and grooves 418. Rotation of lever 75 relative to handle 85 causes each tooth 419 to pass the barb 412 at the same relative height. With the teeth 419 and with the barb 412 of the leaf spring 400 at a similar angle when the barb 412 is mated into a groove 418 between teeth 419, the teeth 419 can still ride pass the barb 412 in the direction of the barb such that further movement of the prove arms 306, 308 toward each other is obtained. However, movement in the opposite direction is not obtainable.

The camming lever or latching means pivot arms 440 has an integral post 442 intermediate its trigger end 450 and its cammed bearing end 451. The post 442 fixes the camming lever bearing end 451 adjacent the resilient strip 400 at a location adjacently forward the leaf spring fixing surface 401 towards the free end of resilient strip 400. Bearing end 451 of camming lever 440 has two distinct intersecting planar bearing faces 444 and 446. With pivot arm 440 positioned as in FIG. 3a with bearing face 444 abutting resilient strip 400, the lever arm 75 and it transverse elongate arm 416 are freely movable with respect to resilient strip 400 and without barb 412 engaging the teeth 419 and grooves 418 of the transverse elongate arm 416. Upon advancing the camming lever 400 to the position 440F the bearing face 446 is brought into coplanar abutting contact with resilient strip 400 thereby causing the strip 400 to be resiliently deformed with its locking barbed element 412 at its free end 408 in engagement with an oppositely located receiver element or groove 418.

It will be appreciated that elongate arm 416 moves upon rotational movement of lever arm 75. As aforementioned, the elongate arm 416 is arranged so that the ratchet comprised of the teeth 418 and groove 419 is brought into a closely adjacent opposed relationship with the resilient strip 400. Either prior to moving the elongate transverse arm 416 adjacent the barb 412 of the leaf spring 400, or with lever arm 75 and its elongate transverse arm 416 in a desired position (which represents a desired position of probe arms 306, 308, the camming lever 440 may be advanced to the position 440F to lock the lever arm 75 relative to the handle 85 (and hence to lock the probe arms at a set position). The lever arm 75 and handle 85 may then be squeezed and moved closer together if desired, with the barb 412 riding over each tooth 419 and into another groove 418. Each locking position corresponds to a respective position of the probe arms 306, 308 (two such positions being indicated in FIGS. 3a and 3b). However, unless the camming lever is returned to position 440, barb 412 will not disengage from the ratchet 499 in the transverse arm 416 to permit the probe arms to move away from each other.

The essence of this first embodiment is an adjustable electrode mounted between the distal ends of two arms of an electrocautery probe whereby the morphology of the electrode is adjusted by moving the distal ends of the probe arms closer together or farther apart. Therefore, in accordance with this embodiment, the probe arms 306, 308 may take many forms other than the pivoting arms described above and the means for moving the arms together or apart may take many forms other than the scissor arms described above. Alternative embodiments of the arms and means for moving them are described in more detail below with reference to FIGS. 7a-7d.

Moreover, in this first embodiment where an adjustable electrode is mounted between the distal ends of two arms of an electrocautery probe, the electrode may take many forms. Different types of electrodes suitable for use with this embodiment of the probe are shown in FIGS. 4-6.

Figure 4A:
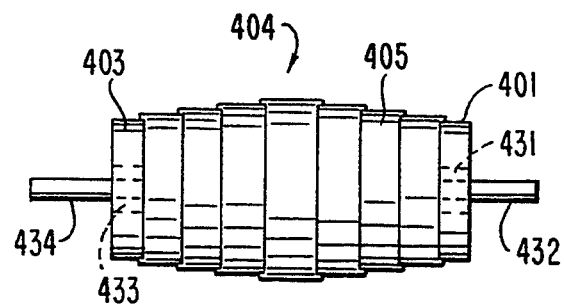
FIGS. 4a and 4b are side and cross section views of a telescoping cylinder electrode useful for the embodiment of FIG. 3.
Figure 4B:
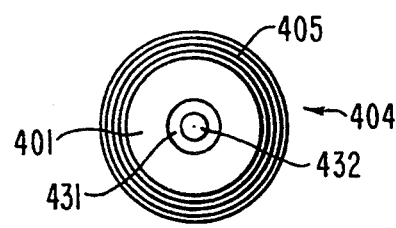

Referring now to FIGS. 4a and 4b, an electrode 404 is shown in side and cross-sectional views. Electrode 404 comprises a plurality of concentric hollow telescoping tube sections 405. The tube sections 405 are so arranged for electrode 404 to collapse and expand in a manner as shown in FIGS. 3a and 3b with electrode 304. Thus, the tube sections 405 are connected to each other by flaring lips (not shown) or in another manner whereby they will not come apart while mounted to the probe and whereby an axial or otherwise appropriate electrode connection may be made. Moreover, it may be advantageous to spring load the assembly of tube sections 405 so they are biased to an expanded configuration as shown in FIG. 4a. Also, as mentioned above, it is preferable that the electrode be mounted for rotation, although this is not absolutely necessary to the invention. Thus, electrode leads 432, 434 are coupled to end portions 401, 403 of the electrode 404 by means of roller bearings or bushings 431, 433 or other means obvious to those of ordinary skill in the art. It will be appreciated that, alternatively, the electrode leads 432, 434 may be fixedly coupled to the electrode and rotatably coupled to the probe arms in order to effect rotation of the electrode.

Figure 5A:
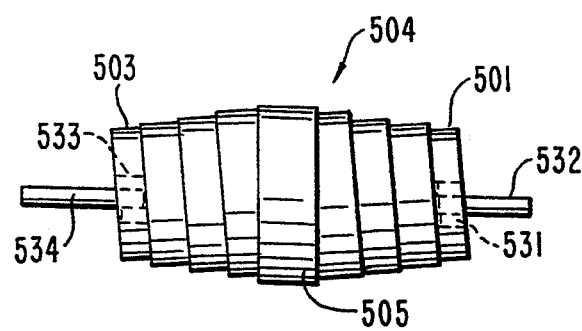
FIGS. 5a and 5b are side and cross section views of a volute spring electrode useful for the embodiment of FIG. 3.
Figure 5B:
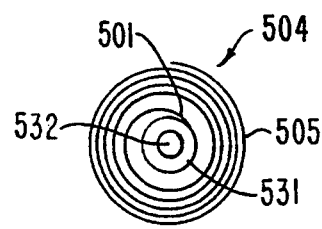
Figure 6:
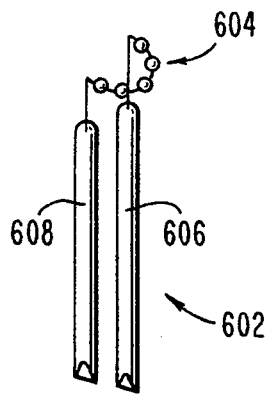
FIGS. 6, and 6a and 6b are respectively a perspective and plan views of a multiple roller ball or springy wire electrode useful for the embodiment of FIG. 3.

An alternative embodiment of the electrode is shown in FIG. 5a and 5b. In this embodiment, the electrode 504 is constructed of a conductive volute spring 505 which provides a similar appearance in FIG. 5a as the tube segments shown in FIG. 4a. A side view, FIG. 5b, however, reveals that the spring 505 comprises a single piece of conductive material wound in a spiral. In the embodiment of FIG. 5, the construction of the electrode from a single piece of conductive material eliminates the need to be concerned about pieces staying together and insofar as the electrode is constructed as a volute spring it is by its construction biased in an expanded configuration as shown in FIG. 5a. As with the embodiment of FIG. 4, though, it is still necessary to provide means for attaching the electrode at its ends 501, 503 to electrode leads 532, 543 and mounting it on the probe arms, and this may be done if desired via direct mounting (e.g. by soldering) or via indirect mounting such as by use of roller bearings or bushings 531, 533.

The electrodes 404 and 504 used with the probe embodiment of FIG. 3 take a form similar to a "roller bar" electrode mentioned in the Background of the Invention. However, the longitudinal size of the roller bar of FIGS. 4 and 5 is adjustable. In adjusting the size of the electrodes, the shape of the electrode is also somewhat changed since in its compressed form it is most nearly a circular cylinder and in its expanded form, it is slightly tapered from the center to the ends. Clearly the amount of taper can be controlled during construction of the electrode so that the expanded electrode can be virtually a cylinder (i.e. no taper) or can be substantially conical, depending on the desired application. Also since a relatively small electrode is desirable when ablating the acute corners of the uterine cavity (102 in FIG. 1), the electrode configuration shown in FIG. 3b is ideal for this purpose. When ablating the broader portions of the uterine cavity (104, 106 in FIG. 1), however, the electrode configuration shown in FIG. 3a is more efficient.

Figure 6A:
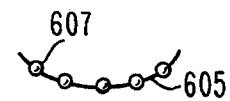
Figure 6B:

FIGS. 6, 6a and 6b show another type of electrode 604 which may be used with a probe 602 having two movable arms 606, 608 between which the electrode 604 is mounted. FIG. 6 shows a perspective view of the electrode 604 mounted on the distal ends of probe arms 606, 608. Electrode 604 comprises a plurality of balls 607 mounted (preferably rotatably mounted) on a springy wire 605 so that when the ends of the wire are brought close together the electrode has an arcuate or semi-circular relatively rigid form as shown in FIG. 6b; and when the ends of the wire 605 are spread apart, the electrode 604 is a nearly straight line as shown in FIG. 6a. When the balls 607 are mounted for rotation about the wire 605, this embodiment is similar to a "roller ball" electrode except that this electrode is adjustable to cover a small or relatively large area. When the electrode wire 605 is compressed as shown in FIG. 6b, the effective operating surface of the electrode is relatively small and similar to a single roller ball electrode, but when the electrode wire is expanded as shown in FIG. 6a, the operating surface of the electrode is relatively broad and acts like several roller ball electrodes operating side by side. Clearly, the number and size of balls 607 will provide for different results and may be varied according to the desired application.

All of the electrode embodiments discussed above involve a probe having two arms and the electrode mounted between the distal ends of the arms where the morphology of the electrode is adjusted by moving the distal ends of at least one of the two probe arms together or apart with adjustment means.

Having described and illustrated several different embodiments of an adjustable electrode mountable on probe arms and adjusted by movement of the probe arms relative to each other, it will be appreciated that many other embodiments of electrodes may be conceived with the knowledge and understanding of the principles disclosed herein. Thus, FIGS. 7a-7b, disclose different embodiments of probe arms and adjustment means for moving the probe arms.

Figure 7A:
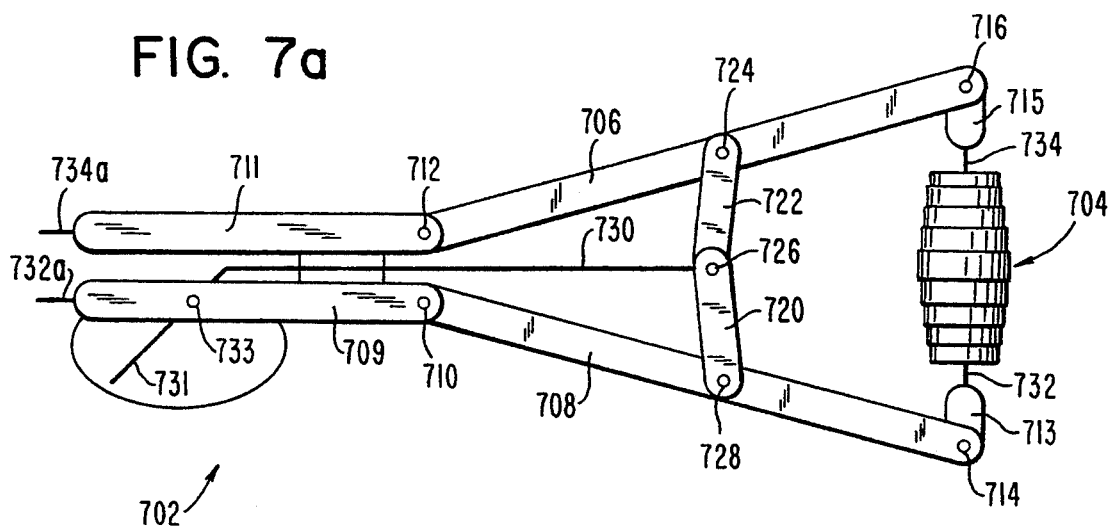
FIGS. 7a–7h are schematic side views of four different means for adjusting the variable morphology electrode of FIGS. 4–6 with the electrodes and adjusting means shown in open and closed positions.
Figure 7B:
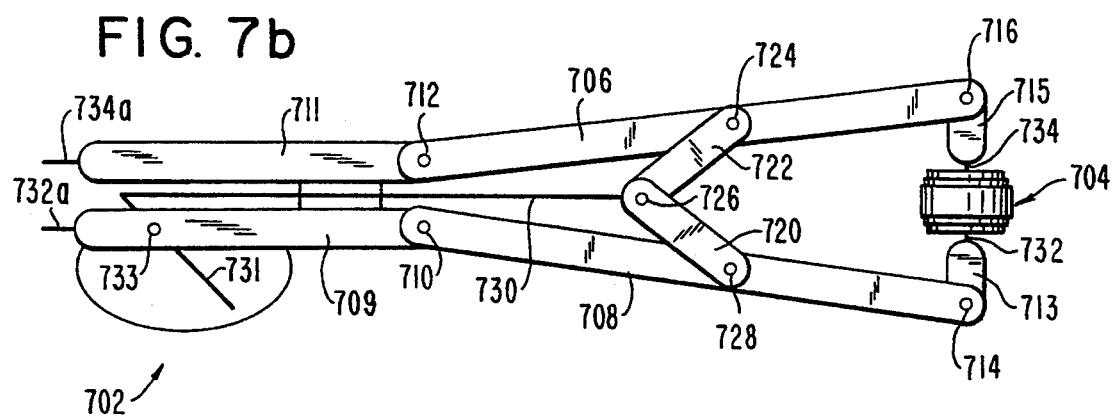

Referring now to FIGS. 7a and 7b, the electrocautery probe 702 comprises two arms 706, 708 having a pivot point 710 near their proximal ends 711, 709. The distal ends 715, 713 of the arms 706, 708 are provided with additional pivot points 716, 714. Telescoping electrode 704 is mounted for rotation between the distal ends 715, 713 of the arms 706, 708 and coupled with electrode leads 734,732. The electrode leads 734, 732 are insulated from and fed through the arms 706, 708 to voltage connections 734a, 732a at the proximal ends 711, 709 of the arms 706, 708. Electrode 704 is adjusted by movement of the distal ends 715, 713 of arms 706, 708 relative to each other. Movement of the distal ends of the arms in this embodiment is accomplished by links 722, 720 pivotally mounted at 724,728 on arms 706, 708 and pivotally mounted to each other at pivot point 726 of actuation rod or member 730. The actuation member 730 is attached to the links pivot point 726 and passes between arms 706, 708 to their proximal ends 711, 709 where actuation member 730 is connected to a lever means 731 having pivot point 733 near the proximal end of the arms.

Movement of the lever means 731 about its pivot point 733 causes member 330 to move the pivot point 726 of links 722,720 thereby moving arms 706, 708 closer together or farther apart. Movement of arms 706, 708, in turn, causes electrode 304 to telescope in or out as respectively shown in FIGS. 7a and 7b thereby changing the morphology of electrode 704.

Figure 7C:
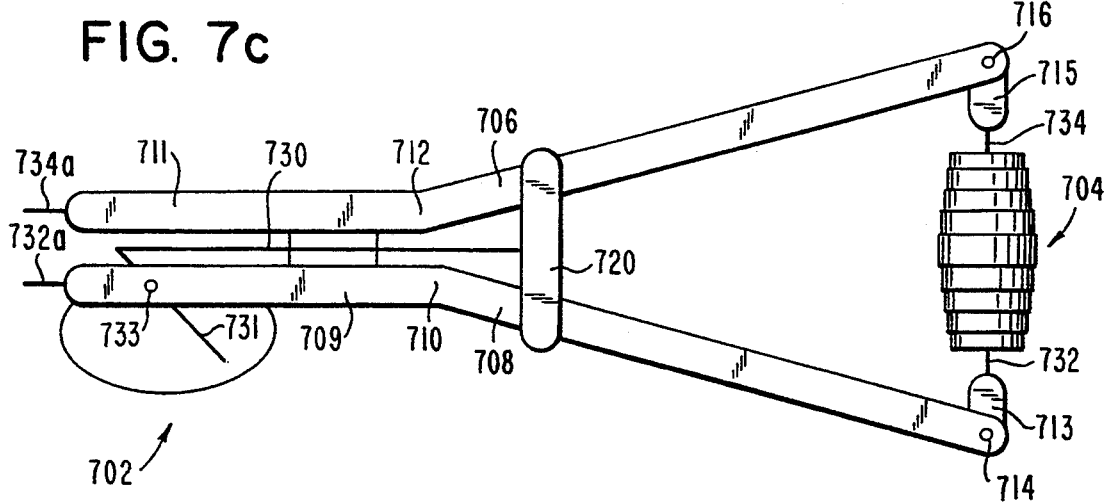
Figure 7D:
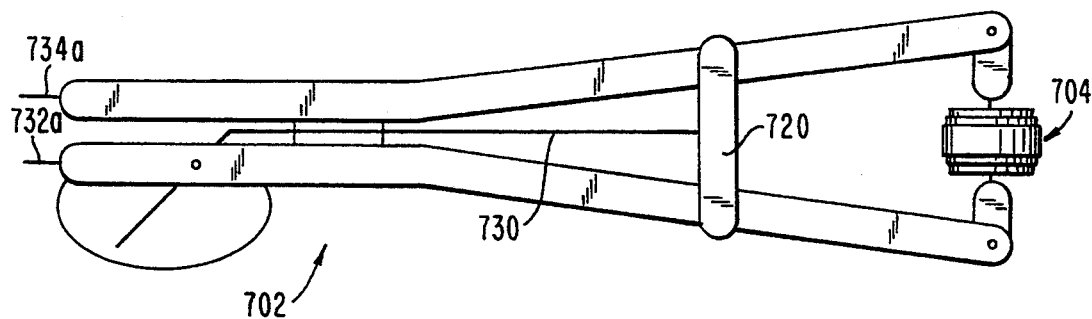

Referring now to FIG. 7c, the electrocautery probe 702 has two resilient arms 706, 708 each having a proximal ends 711, 709 and respective distal ends 715, 713. Each arm 706, 708 is provided with a preferably continuous springy bend 712,710 so that their distal ends 715, 713 are biased apart from each other. An electrode 704 is mounted for rotation between the distal ends 715, 713 of arms 706, 708. The distal ends 715, 713 of the arms are advantageously provided with pivot points 716, 714. Electrode 704 is coupled with electrode leads 734,732 which are insulated from and fed through arms 706, 708 to voltage connections 734a, 732a at the proximal ends 711, 709 of arms 706, 708. The electrode is adjusted by movement of the distal ends 715, 713 relative to each other. In the embodiment of FIGS. 7c and 7d, movement is effected by a sliding ring 720 which encircles arms 706, 708 and is slidable from a position nearer the springy bends 712,710 of the arms to a position nearer the distal ends 715, 713 of the arms. The diameter of the ring 720 and its material are chosen so that the ring 720 fits snugly but is still slidable. Ring 720 is attached to an actuating member 730 which is moved by a lever means 713 having a pivot point 733 near the proximal end of the arms. As the ring 720 is moved towards the distal ends of the arms, it biases the arms 706, 708 against their springy bends 712,710 to move the distal ends 715, 713 closer together as shown in FIG. 7d. As the ring is moved away from the distal ends of the arms, the springy bends 712, 710 bias the arms apart as shown in FIG. 7c.

Figure 7E:
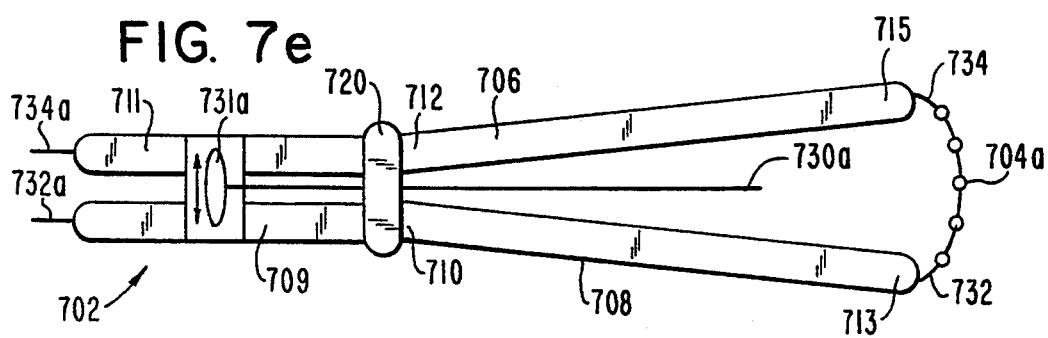
Figure 7F:
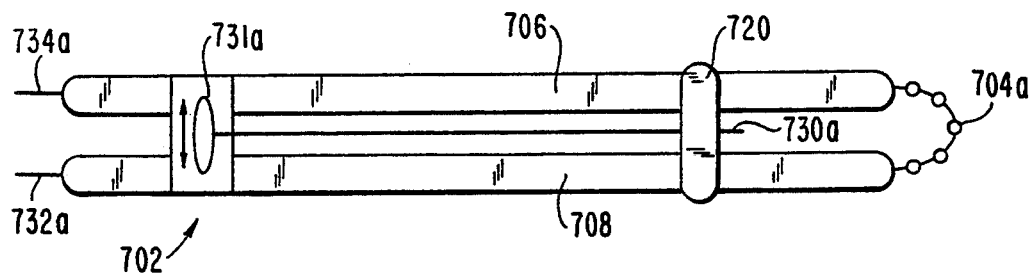

FIGS. 7e and 7f show another embodiment similar to the embodiment shown in FIGS. 7c and 7d. In this embodiment, the distal ends of arms 706, 708 are not provided with pivot points because the electrode 704a (compare FIG. 6) does not require them. The arms 706, 708 are provided, however, with springy bends 712,710 and a sliding ring 720. In this embodiment, the ring 720 is threadably mounted on a rotatable threaded shaft 730a which is rotated by a thumb wheel 731a near the proximal ends 711, 709 of the arms. Rotation of the shaft 730a moves ring 720 towards the the distal or proximal ends of the probe effecting the same action as described in reference to FIGS. 7c and 7d.

Figure 7G:
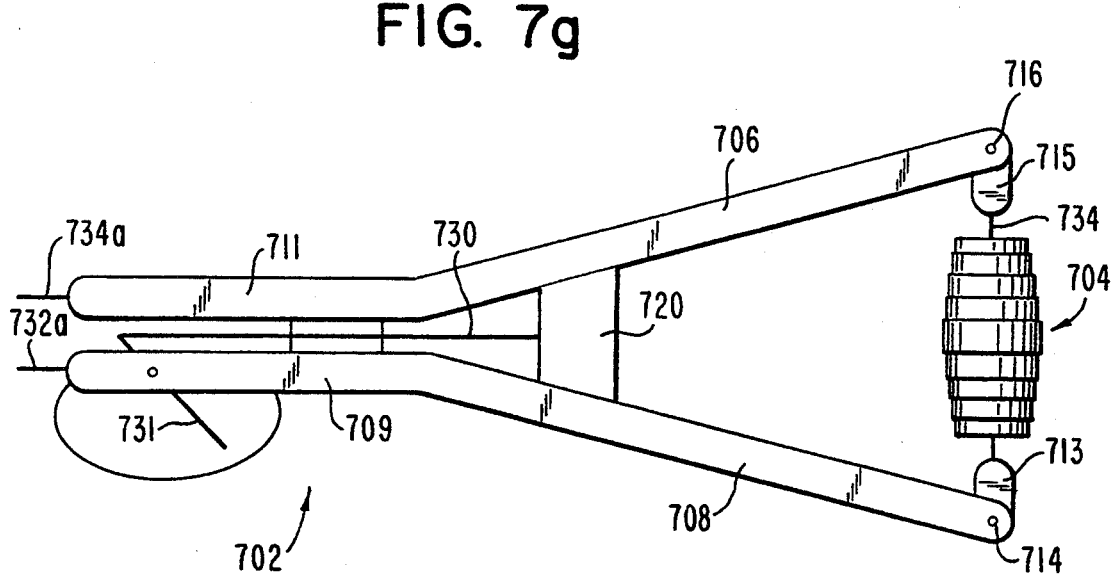
Figure 7H:
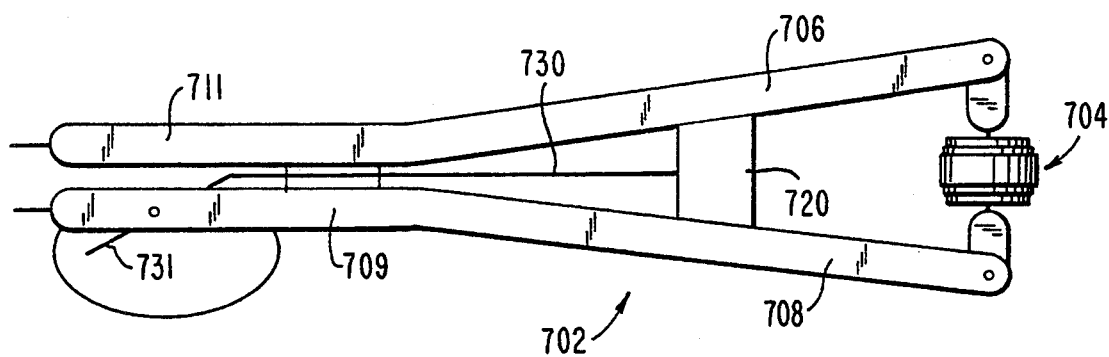

FIGS. 7g and 7h show another embodiment similar to the embodiment shown in FIGS. 7c and 7d. In this embodiment, arms 706, 708 are provided with springy bends 712, 710 so that their distal ends 715, 713 are biased towards each other. Movement of arms 706, 708 is effected by a sliding wedge 720 attached to a slidable member 730 which is moved by a lever means 713 having a pivot point 733 near the proximal end of the arms. As the wedge 720 is moved toward the proximal ends of the arms, it biases the arms 706, 708 against their springy bends 712, 710 to move the distal ends 715, 713 apart as shown in FIG. 7g. As the wedge is moved toward the distal ends of the arms, the springy bends 712, 710 bias the arms together as shown in FIG. 7h.

Having described and illustrated several different embodiments of mechanisms for adjusting the morphology of the electrodes, it will be appreciated that many other embodiments of such mechanisms could be conceived with the knowledge and understanding of the principles disclosed herein.

Figure 8A:
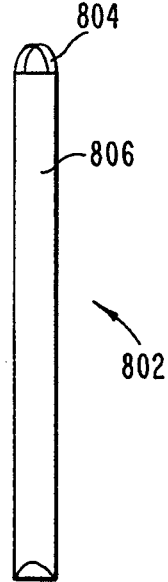
FIGS. 8a–8b are schematic open and closed side views of another embodiment of the invention where the electrode changes morphology by movement into and out of a hollow cylinder.
Figure 8B:
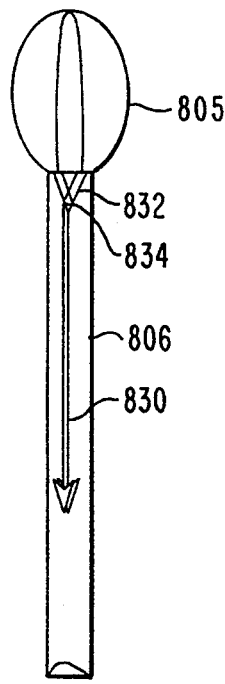
Figure 9A:
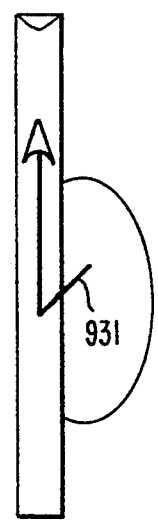
FIGS. 9a–9b are schematic side views of means for adjusting the electrodes in the embodiments of FIGS. 8a–8i.
Figure 9B:
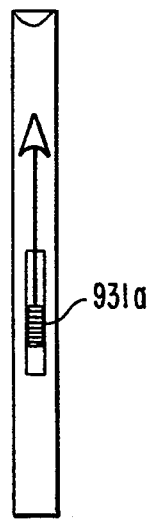

FIGS. 8a–8i show different related embodiments of the probe. In FIGS. 8a and 8b, the probe 802 comprises a single hollow cylinder 806 and the electrode 804 comprises a plurality of loops 805 of springy wire to form a whisk-like structure with enough resiliency so that it may be compressed when inserted into the cylinder 806 (FIG. 8a) and expand when pushed out from the cylinder 806 (FIG. 8b). The electrode 804 is provided with electrode connections 832,834 for connection with a cauterizing voltage source which is provided by conductors inside the cylinder 806. The means for adjusting the electrode in this embodiment is simply the coaction of the cylinder 806 with the electrode 804 as the electrode is moved in and out of the cylinder. Movement of the electrode in this respect is accomplished by means 830 which comprises a relatively rigid member slidably mounted within the cylinder 806 and connected to the electrode 804 such that movement of the member 830 moves the electrode into and out of the cylinder 806. FIG. 8b shows the member 830 schematically with an arrow pointing towards the proximal end of the probe. Movement of the member 830 may be effected by a lever means or other means or may be effected simply by extending the length of the member beyond and through the proximal end of the probe. FIGS. 9a and 9b schematically show two possible means for moving member 830 such as lever means 931 or thumb slide 931a. Another such means was disclosed with reference to the push rod of FIG. 3.

Returning to FIG. 8a it is seen that the electrode 804 is pulled into the cylinder 806 in which configuration the electrode assumes the size and shape of small semicircular wires. By pushing the rigid member 830 towards the distal end of the probe, the electrode 804 is pushed out of the cylinder 806 and expands to a configuration having the size and shape of several loop electrodes as shown in FIG. 8b.

FIGS. 8c–8g show yet another embodiment of probe and electrode and while this embodiment of the probe 802 comprises two arms 806 and 808, the electrode 804 is not adjusted by moving the arms together or apart. In this embodiment, the electrode 904 is adjusted in a manner similar to the embodiment of FIGS. 8a and 8b.

Figure 8C:
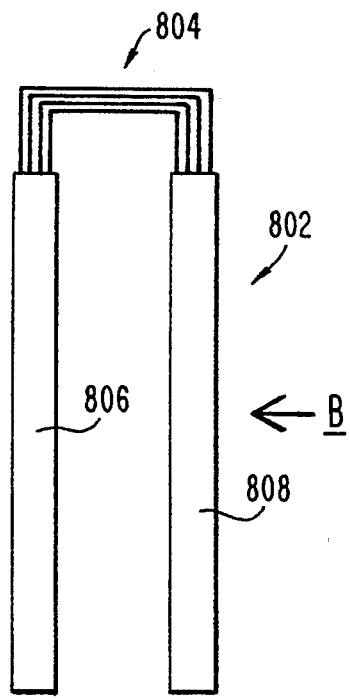
FIG. 8c and 8d are schematic side views of another embodiment of the invention with the electrode adjusted to closed and open positions respectively.
Figure 8D:
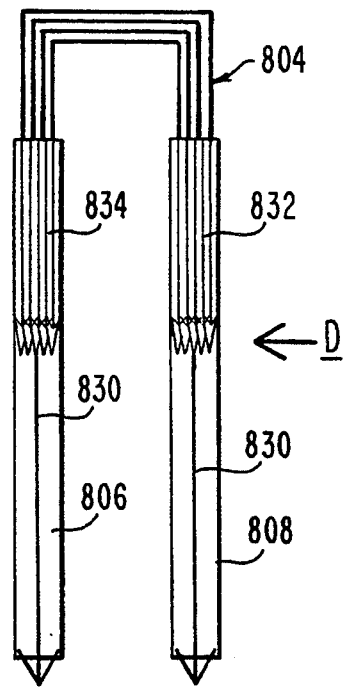
Figures 8E, 8F:
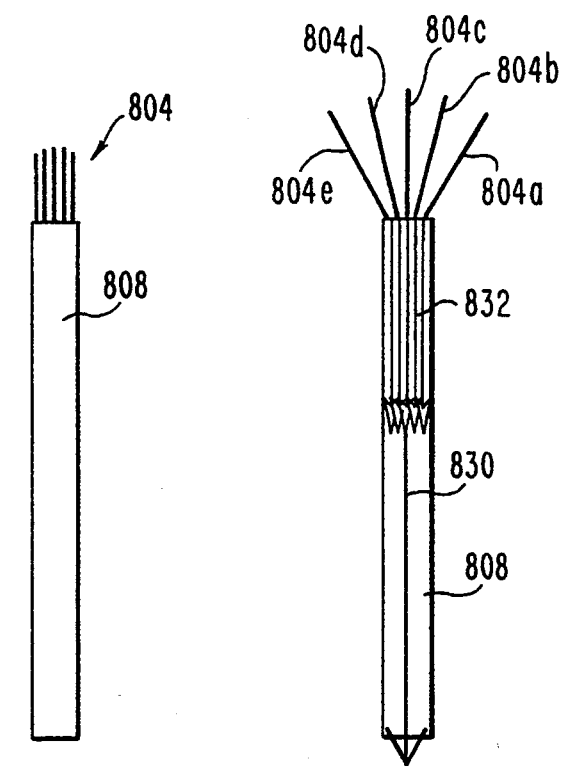
FIG. 8e and 8f are schematic side views of the embodiment of FIG. 8c and 8d looking in the direction of the arrows B and D respectively thereof.
Figure 8G:
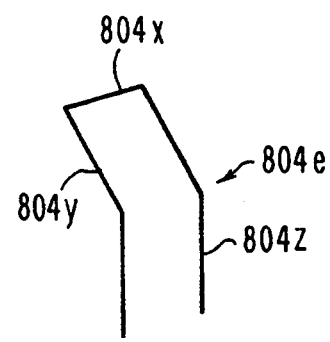
FIG. 8g is a perspective view of a portion of the electrode used in the embodiment of FIGS. 8c–8f.

Probe 802 comprises two parallel arms 806 and 808 which are hollow cylinders. The cylindrical arms may have a circular cross section or a rectangular cross section or some other cross section depending on the exact construction of electrode 804. In the embodiment shown, a circular or rectangular cross section is intended. The electrode 804 comprises a plurality of C-shaped conductors 804a–804e arranged parallel to each other and inserted into cylinders 806 and 808 as shown. Although FIGS. 8e and 8f show five such C-shaped conductors, any number may be used depending on the size of the probe and the thickness of the conductors. For reference, the C-shape of the conductors may be considered as having a connecting section 804x, and two leg sections 804y and 804z. At least one of the conductors, for example 804e, shown in perspective at FIG. 8g, is formed with a springy bend in its legs 804y and 804z. In the embodiment shown, conductor 804a has a similar bend and conductors 804b and 804d have similar but lesser bends and conductor 804c has no bend. All of the conductors are connected at or near the end point of their legs and are connected to leads 832, 834.

The means for adjusting electrode 804, like the embodiment of FIGS. 8a and 8b, is the coaction of the cylinders 806, 808 with the electrode 804 as the electrode is moved in and out of the cylinders. Movement of the electrode in this respect is effected by means 830 which comprises a pair of relatively rigid members slidably mounted within the cylinders 806, 808 and connected to the electrode 804 such that movement of the members 830 moves the electrode into and out of the cylinders 806, 808. FIGS. 8c and 8d show the electrode 804 pulled into the cylinders in which configuration the electrode assumes the size and shape of a small loop. By pushing the rigid members 830 towards the distal end of the probe (using means such as those shown, e.g. in FIGS. 9a or 9b), the electrode 804 is pushed out of the cylinders and expands to a configuration having the size and shape of several larger loop electrodes spread apart in a fan-like configuration. The spreading of the electrode is seen in FIG. 8f and it will be appreciated how the bend discussed in reference to FIG. 8g effects this spreading.

Figure 8H:
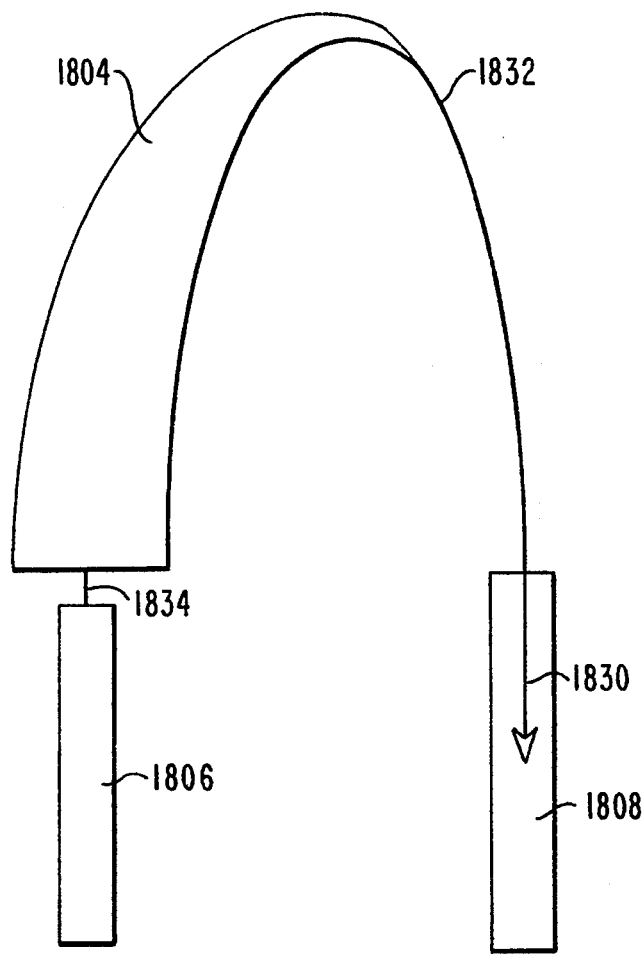
FIGS. 8h and 8i are schematic side views of another embodiment of the invention.
Figure 8I:
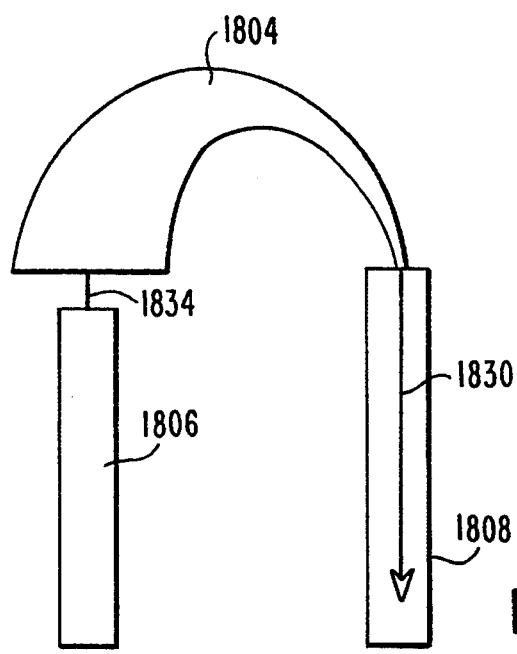

FIGS. 8h and 8i show yet another embodiment of electrode 1804 and probe 1802, again having two arms 1806 and 1808 but where the electrode 1804 is not necessarily adjusted by moving the arms relative to each other. In this embodiment, electrode 1804 is a band of varying width (such as a metal band of decreasing width which terminates by soldering, welding or fitting to a wire) attached to leads 1832, 1834 and probe arm 1808 is a hollow cylinder. Probe arm 1806 need not be a cylinder and need not be hollow so long as electrode lead 1834 can pass through it in a manner as described in reference to the other embodiments. Lead 1832 is attached to or comprises part of means 1830 for moving the electrode into and out of cylindrical probe arm 1808. Means 1830 for moving the electrode may comprise any known means or any of the means discussed above. FIG. 8h shows the electrode 1804 in its expanded configuration where it has a large size and broad shape and FIG. 8i shows the electrode 1804 partially pulled into cylindrical probe arm 1808 whereby the electrode has a smaller size.

There have been described and illustrated herein several embodiments of an electrocautery probe having an electrode of variable morphology electrode. While particular embodiments of the invention have been described, it is not intended that the invention be limited thereto, as it is intended that the invention be as broad in scope as the art will allow and that the specification be read likewise. Thus, while particular means for moving probe arms together and apart have been disclosed, it will be appreciated that other means could be utilized. Moreover, while these means have been described as moving probe arms together and apart, means which move the probe arms in only one direction could be used resulting in the limitation that the electrode could be adjusted in only one direction. In addition, while it has been described that the distal ends of both arms move, constructions in which only one of the arms moves will readily suggest themselves. Also, while several types of adjustable electrodes have been shown, it will be recognized that other types of electrodes could be used with the probe arms of the invention with similar results obtained. In addition, while several embodiments of cylindrical probes have been described, it will be appreciated that cylinders of different configuration and cross section could be used; and while several embodiments of electrodes for use with cylindrical probes have been disclosed, it will be appreciated that other types of electrodes could be used with the cylindrical probes to achieve the same results in substantially the same manner. It will therefore be appreciated by those skilled in the art that yet other modifications could be made to the provided invention without deviating from its spirit and scope as so claimed.

I claim:

1. An electrocautery probe, comprising:
   a) a first and second probe arm each having a distal end and a proximal end;
   b) an electrode of variable morphology mounted between said distal ends of said first and second probe arm;
   c) voltage supply means coupled to said electrode for supplying an electrical potential to said electrode; and
   d) actuation means coupled to at least one of said first and second probe arm for moving at least one of said distal ends relative to the other of said distal ends,
   wherein the morphology of said electrode is changed when at least one of said distal ends is moved.

2. An electrocautery probe according to claim 1, wherein:
   said electrode is mounted along a mounting axis substantially perpendicular to an axis of said actuation means and said electrode rotates around said mounting axis.

3. An electrocautery probe according to claim 1, wherein:
   said electrode comprises a volute spring.

4. An electrocautery probe according to claim 1, wherein:
   said electrode comprises a plurality of concentric mating telescoping tube sections.

5. An electrocautery probe according to claim 1, wherein:
   said electrode comprises a resilient wire and a plurality of balls mounted on said wire.

6. An electrocautery probe according to claim 1, wherein:
   said first probe arm comprises a resilient member diverging from said second probe arm, and
   said means for moving comprises a slidable ring encircling both of said probe arms.

7. An electrocautery probe according to claim 6, wherein:
   said means for moving further comprises a slidable member connected to said slidable ring.

8. An electrocautery probe according to claim 6, wherein:
   said means for moving further comprises a rotatable threaded member threadably connected to said slidable ring.

9. An electrocautery probe according to claim 1, wherein:
   said means for moving includes means for moving said first and second distal ends.

10. An electrocautery probe according to claim 9, wherein:
    said first probe arm is provided with a first pivot point between said first distal end and said first proximal end whereby said first distal end pivots relative to said first proximal end,
    said second probe arm is provided with a second pivot point between said second distal end and said second proximal end whereby said second distal end pivots relative to said second proximal end, and
    said means for moving comprises a first link means pivotally connected to said first probe arm between said first pivot point and said first distal end a second link means pivotally connected to said second probe arm between said second pivot point and said second distal end, said first and second link means being pivotally connected to each other at a pivot point such that movement of said pivot point moves said first and second distal ends relative to each other.

11. An electrocautery probe according to claim 10, wherein:
    said means for moving comprises a slidable member connected to said pivot point.

12. An electrocautery probe according to claim 10, wherein:
    said means for moving further comprises a rotatable threaded member threadably connected to said pivot point.

13. An electrocautery probe according to claim 9, wherein:
    said first probe arm comprises a resilient member diverging from said second probe arm,
    said second probe arm comprises a resilient member diverging from said first probe arm,
    whereby said first and second distal ends are biased to a position away from each other, and
    said means for moving comprises a slidable ring encircling both of said probe arms.

14. An electrocautery probe according to claim 13, wherein: said means for moving further comprises a slidable member connected to said slidable ring.

15. An electrocautery probe according to claim 13, wherein:
    said means for moving further comprises a rotatable threaded member threadably connected to said slidable ring.

16. An electrocautery probe according to claim 1, further comprising:
    e) a hollow tube having a proximal end and a distal end; and
    f) a push rod having a proximal end and a distal end and extending through said hollow tube,
    said first and second probe arm being coupled to said distal end of said hollow tube,
    said at least one of said first and second probe arm being coupled to said distal end of said push rod,
    said actuation means being coupled to said proximal end of said hollow tube and to said proximal end of said push rod for imparting reciprocal axial movement of said push rod relative to said hollow tube.

17. An electrocautery probe according to claim 16, further comprising:
    g) clevis means for coupling said at least one of said first and second probe arm to said distal end of said hollow tube,
    said at least one of said first and second probe arm being coupled to said clevis means at a pivot point, said pivot point being intermediate of said proximal end and said distal end of said at least one of said first and second probe arm, said proximal end of said at least one of said first and second probe arm being coupled to said distal end of said push rod.

18. An electrocautery probe according to claim 17, wherein:

the other of said first and second probe arm is coupled to said clevis means at a pivot point, said pivot point being intermediate of said proximal end and said distal end of said other one of said first and second probe arm, said proximal end of said other one of said first and second probe arm being coupled to said distal end of said push rod.

19. An electrocautery probe according to claim 16, wherein:

said voltage supply means comprises a terminal connector coupled to said hollow tube.

20. An electrocautery probe according to claim 16, wherein:

said actuation means comprises a handle member fixedly coupled to one of said hollow tube and said push rod, and a lever member pivotally coupled to said handle member and coupled to the other of said hollow tube and said push rod.

* * * * *